United States Patent [19]

Bokros et al.

[11] 3,952,334

[45] Apr. 27, 1976

[54] BIOCOMPATIBLE CARBON PROSTHETIC DEVICES

[75] Inventors: Jack C. Bokros; Jere B. Horsley, Jr., both of San Diego, Calif.

[73] Assignee: General Atomic Company, San Diego, Calif.

[22] Filed: Nov. 29, 1974

[21] Appl. No.: 527,971

[52] U.S. Cl.............................. 3/1; 3/1.5;
3/1.9; 128/92 C; 128/92 BC; 128/1 D;
427/407; 427/409; 32/10 A
[51] Int. Cl.² .................... A61F 1/24; A61F 1/22
[58] Field of Search............ 3/1, 1.5, 1.7, 1.9–1.913;
128/92 C, 92 CA, 92 R, 92 BC, 1 D; 32/10 A

[56] References Cited
UNITED STATES PATENTS

| | | | |
|---|---|---|---|
| 3,546,711 | 12/1970 | Bokros | 3/1.5 |
| 3,579,645 | 5/1971 | Bokros | 3/1.5 |
| 3,685,059 | 8/1972 | Bokros et al. | 3/1 |
| 3,707,006 | 12/1972 | Bokros et al. | 128/92 C |
| 3,797,113 | 3/1974 | Brainin | 32/10 A |
| 3,849,887 | 11/1974 | Brainin | 32/10 A |

*Primary Examiner*—Ronald L. Frinks
*Attorney, Agent, or Firm*—Fitch, Even, Tabin & Luedeka

[57] ABSTRACT

A biocompatible prosthetic device comprising a metal alloy substrate, an intermediate layer of a high-temperature polymer which is strongly bonded thereto, and an exterior coating of dense vapor-deposited carbon. The carbon layer is thromboresistant and strongly adheres to the intermediate layer which in turn strongly adheres to the metal alloy. The polymer may be the reaction product of pyromelletic dianhydride and a diaminodiphenyl ether, and the carbon may be deposited under high vacuum conditions from a suitably heated carbon source, e.g., by ion-plating or vacuum vapor deposition.

11 Claims, No Drawings

BIOCOMPATIBLE CARBON PROSTHETIC DEVICES

This invention relates to prosthetic devices and more particularly to the manufacture of prosthetic devices and/or parts therefor utilizing metal substrates by applying strongly adherent, biocompatible carbon coatings thereupon.

The employment of pyrolytic carbon coatings to produce biocompatible and thromboresistant surfaces for prosthetic devices is known and is described in U.S. Pat. Nos. 3,526,005, issued Sept. 1, 1970, and 3,685,059, issued Aug. 22, 1972, which patents generally describe such deposition of pyrolytic carbon coatings, usually from a diluted hydrocarbon atmosphere at atmospheric pressure. Various other techniques have been developed for depositing carbon coatings, for example as by vacuum vapor deposition (VVD) which is also sometimes referred to as vacuum metalizing or physical vapor deposition or evaporative coating. Coatings deposited by such VVD techniques show promise as coatings for prosthetic devices; however, when certain substrate materials are coated, the resultant bond between coating and substrate has not been in all respects satisfactory. Accordingly, methods of applying more adherent carbon coatings of this general type are desired.

It is the object of the present invention to provide a method of making prosthetic devices having strongly adherent, vapor-deposited carbon coatings. A further object of the invention is to provide prosthetic devices having strongly adherent, biocompatible and thromboresistant carbon coatings. Still another object is to provide a method for producing prosthetic devices using VVD techniques which have biocompatible and thromboresistant carbon-coated exterior surfaces. These and other objects of the invention will be readily apparent from a reading of the following detailed description of methods for making prosthetic devices embodying various aspects of the invention.

It has been found that substrates, particularly certain metal alloys, to which vapor-deposited carbon cannot be readily adhered as a uniform continuous layer, can be first pre-coated with an organic polymer, such as a high molecular weight linear polymer or suitable precursor of a thermosetting polymer. Once the polymer is set to provide an intermediate layer, a uniform, strongly adherent carbon coating can be deposited thereon to create a prosthetic device. The various so-called "high-temperature polymers" which have generally been developed in the last decade are preferred, and generally those resins with the highest softening points are the most preferred. The particularly preferred class of these polymers are polyimides which can be applied as a solution and then cured in situ to form an infusible polymer. For purposes of this application, the term prosthetic device is intended to include not only bone, intravascular, and valve prostheses, and parts thereof, but also includes parts for extracorporeal devices which will be in contact with the bloodstream of a living person, for example, circulatory assist devices and the like.

Various metal alloys, for example stainless steels, cobalt alloys such as Haynes alloy number 25 and Vitallium, and the like, show sufficient corrosion resistance to permit their use in the construction of prosthetic devices. Moreover, such metal alloys have the desired tensile strength for applications where such strength is needed, for example, in bone repair or replacement and the like. However, problems have developed with the compatibility of these alloys and the body organs, tissue and blood with which they would come into contact if used in the construction of prosthetic devices. However, carbon, the organic building block for all body matter, has shown outstanding tissue and blood compatibility for a variety of prosthetic device applications. By the present pre-coating method, these corrosion-resistant metal alloys can now be provided, by ion-plating or VVD coating techniques, with strongly adherent carbon coatings.

It has been found that certain high-temperature polymer layers can be applied to these corrosion-resistant metal alloys which will strongly bond thereto when cured in situ. As a result, an intermediate layer is provided which is excellently receptive to the vapor deposition thereupon of a dense, biocompatible carbon layer. The polymer solution may be applied in any suitable manner, as by dipping, spraying, painting, or the like, which provides a smooth surface. The polymer chosen will normally be soluble in an organic solvent so that it can be applied as a liquid solution. In the preferred case of a polyimide, the solvent is preferably removed prior to the in situ curing to form the infusible polymer. By the initial removal of the solvent, a thin surface film forms prior to the creation of the final, infusible polymer, and smoother resultant surface is obtained.

These high-temperature polymers exhibit thermal stability at temperatures of 300°C. and higher and are generally characterized as linear, high molecular weight, aromatic, nitrogen-linked polymers. Examples of such high-temperature polymers include ordered aromatic copolyamides, such as the reaction product of phenylenebis (amino-benzamide) and isophthaloyl chloride, all-aromatic polybenzimidazoles, such as poly [2,2'(m-phenylene)-5,5'(6,6' benzimidazole)], polyoxadiazoles, poly(N-phenyl triazoles), polybenzobenzimidazoles, polyimides and poly(amide-imide) resins.

The preferred polymers are polyimide and poly (amide-imide) resins. Polyimides are predicated upon the initial condensation reaction between an aromatic diamine, such as a diaminophenyl ether, with an aromatic dianhydride, such as pyromelletic dianhydride. The resultant, tractable polyamic acid is converted, during final cure, to an infusible, insoluble and intractable polyimide as a result of the loss of water. The polyimides can be applied in the form of the tractable polyamic acids dissolved in a suitable organic solvent, such as pyridine, dimethylacetamide or N-methylpyrolidone. As indicated above, the solvent is preferably removed prior to the final heat cure which drives off the water and produces the intractable polyimide. The poly(amide-imide) resins are similar in chemical structure and may also be applied, in a polar solvent, in the amic acid form and subsequently curved to the insoluble, intractable form by thermally causing the loss of water.

As earlier indicated, application of the polymer solution can be by immersion, by spraying, by painting or by any other suitable method. The thickness of the cured polymer layer should be at least about 0.1 micron, and it is not considered necessary to use an intermediate layer thicker than about 25 microns. Generally, the polymer layer will be between about 0.2 and about 10 microns thick. Once the application is completed, the solvent is removed, preferably at a temperature below about 100°C. and a smooth, continuous polymer film forms at the surface exposed to the atmosphere. Upon the conclusion of solvent removal, the temperature is raised to about 130°C.–150°C., and a final curing is generally carried out at a temperature of about 225°C. In the final baking process, the soluble, tractable polymer is converted to the insoluble, intractable, infusible polymer by the loss of water.

Following the in situ heat treatment of the polymer layer, the pre-coated substrate is ready for the application of the biocompatible carbon coating. The carbon may be applied using standard VVD coating technology, operating at a vacuum of about $10^{-5}$ torr. Ion-plating, another vapor deposition process, is preferred, and may be carried out, for example, at about 10 to 20 microns pressure of argon, helium or some other suitable inert gas. In ion-plating, the substrate is made a high-voltage sputtering cathode and is subjected to a flux of high energy ions from either a heated carbon source or a low pressure hydrocarbon gas during film formation.

The carbon coating should be at least about 1000A (0.1 micron) thick, and usually a thickness of more than about 12,000A is not needed. Generally, a coating thickness of about 4,000 to about 5,000A of dense carbon (at least about 1.6 gram/cm$^3$) is employed. Preferably, the vapor-deposited carbon has a density of at least about 1.8 g/cm$^3$. Not only does such vapor-deposited carbon exhibit biocompatible properties substantially equivalent to that of isotropic pyrolytic carbon, but it also exhibits excellent adherence to the organic polymeric intermediate layer or pre-coating which in turn is strongly bonded to the underlying metal alloy substrate. As a result, the coated and pre-coated substrate exhibits excellent properties for use as a prosthetic device and is considered to be fully acceptable for implantation within the human body as a bone pin or replacement, as a part of a heart valve, a dental implant or the like.

The following Example is exemplary of one method for making a prosthetic device embodying various features of the invention. However, the Example should not be considered to place any limitations upon the invention which is defined solely by the claims at the end of this specification.

EXAMPLE

A valve housing for a Bjork heart valve made of Haynes alloy number 25 (a cobalt-base alloy) is cleaned by ultrasonic cleaning. The cleaned heart valve housing is immersed in a solution of Pyre-M.L., containing about 17 percent solids in an aromatic hydrocarbon solvent, a product of duPont Company. This polymer solution contains polyamic acids formed by the reaction of aromatic diamines, such as 4,4'-Diaminodiphenyl ether, with pyromelletic dianhydrides. The valve housing is removed from the precoating solution, drained and then dried for about 15 minutes at about 110°C. in an air-circulating oven to drive off the major portion of the solvent and form a film at the surface. Heating is continued as the temperature is raised to about 140°C. for about 15 minutes and then to about 225°C. for a final curing period of 60 minutes. Examination of the substrate shows a polyimide uniform continuous coating about 1.5 microns thick over the metal substrate.

The precoated substrate is transferred to an evaporative coater, and a vacuum of $10^{-5}$ torr. is established therein. A crucible within the coater, filled with a commercial grade of artificial graphite, is heated by electron beam bombardment. Coating is carried out until a thickness of about 4500A of carbon is deposited. The carbon-coated valve body is removed from the evaporative coater and examined. The exterior carbon layer is smooth and uniform and has a density of about 2.1 gm/cm$^3$.

Testing of the valve casing establishes that the carbon coating is strongly adherent and can withstand the fluid forces involved. Previous testing had established that vapor-deposited carbon of this density, deposited under these conditions, was thromboresistant and fully compatible with body tissue. The precoated, carbon-coated metal alloy substrate is considered to be excellently suited for use as a valve body for implantation in a human being.

Although the invention has been described with regard to certain preferred embodiments, it should be understood that modifications such as would be obvious to those having the ordinary skill in this art may be made without deviating from the scope of the invention which is defined in the appended claims. For instance, in addition to metal alloy substrates, there may be advantages to employing the intermediate pre-coating with other substrates for prosthetic devices, for example, ceramics, such as aluminum oxide, glass, quartz and the like.

Various features of the invention are set forth in the claims that follow.

What is claimed is:

1. A biocompatible prosthetic device comprising a metal alloy substrate, an intermediate, continuous layer of an organic high-temperature polymer which is strongly bonded thereto, and an exterior in-situ-deposited coating of continuous dense vapor-deposited carbon at least 1000A thick which carbon layer is biocompatible and strongly adherent to said intermediate layer as a result of its in situ vapor deposition.

2. A prosthetic device in accordance with claim 1 wherein said coating is not more than about 12,000A thick.

3. A prosthetic device in accordance with claim 1 wherein said polymer is a polyimide resin.

4. A prosthetic device in accordance with claim 1 wherein said polymer is a poly(amide-imide) resin.

5. A prosthetic device in accordance with claim 3 wherein said polymer is the reaction product of pyromelletic dianhydride and a diaminodiphenyl ether.

6. A biocompatible prosthetic device comprising a substrate, an intermediate continuous layer of an organic high-temperature polymer consisting essentially of a linear high-molecular-weight aromatic nitrogen-linked polymer, said intermediate layer being strongly bonded to said substrate, and an exterior coating at least 1000A thick of continuous, dense vapordeposited carbon, said carbon layer being deposited in situ upon said intermediate layer and thereby strongly adherent thereto.

7. A prosthetic device in accordance with claim 6 wherein said substrate is a metal alloy.

8. A prosthetic device in accordance with claim 7 wherein said high temperature polymer is selected from the group consisting of ordered copolyamides, all-aromatic polybenzimidazoles, polyoxadiazoles, poly(N-phenyl triazoles), polybenzobenzimidazoles, polyimides and poly(amide-imide) resins.

9. A prosthetic device in accordance with claim 7 wherein said polymer is a polyimide resin.

10. A prosthetic device in accordance with claim 7 wherein said polymer is a poly(amide-imide) resin.

11. A prosthetic device in accordance with claim 7 wherein said polymer is the reaction product of pyromellitic dianhydride and a diaminodiphenyl ether.

* * * * *